US008218847B2

(12) United States Patent
Averbuch et al.

(10) Patent No.: US 8,218,847 B2
(45) Date of Patent: Jul. 10, 2012

(54) HYBRID REGISTRATION METHOD

(75) Inventors: Dorian Averbuch, Ramat HaSharon (IL); Oded Zur, Kochav-Ya'ir Zur Yigal (IL); Oren Weingarten, Hod HaSharon (IL)

(73) Assignee: superDimension, Ltd., Herzliya (IL)

( * ) Notice: Subject to any disclaimer, the term of this patent is extended or adjusted under 35 U.S.C. 154(b) by 409 days.

(21) Appl. No.: 12/478,573

(22) Filed: Jun. 4, 2009

(65) Prior Publication Data

US 2010/0034449 A1    Feb. 11, 2010

Related U.S. Application Data

(60) Provisional application No. 61/059,669, filed on Jun. 6, 2008.

(51) Int. Cl.
*G06K 9/00* (2006.01)
(52) U.S. Cl. ..................................................... 382/131
(58) Field of Classification Search .................. None
See application file for complete search history.

(56) References Cited

U.S. PATENT DOCUMENTS

| | | | |
|---|---|---|---|
| 5,480,422 A | 1/1996 | Ben-Haim |
| 5,558,091 A | 9/1996 | Acker et al. |
| 5,729,129 A | 3/1998 | Acker |
| 5,752,513 A | 5/1998 | Acker et al. |
| 5,928,248 A | 7/1999 | Acker |
| 6,016,439 A | 1/2000 | Acker |
| 6,147,480 A | 11/2000 | Osadchy et al. |
| 6,161,032 A | 12/2000 | Acker |
| 6,188,355 B1 | 2/2001 | Gilboa |
| 6,201,387 B1 | 3/2001 | Govari |
| 6,203,493 B1 | 3/2001 | Ben-Haim |
| 6,211,666 B1 | 4/2001 | Acker |
| 6,226,543 B1 | 5/2001 | Gilboa et al. |
| 6,233,476 B1 | 5/2001 | Strommer et al. |
| 6,314,310 B1 | 11/2001 | Ben-Haim et al. |
| 6,332,089 B1 | 12/2001 | Acker et al. |
| 6,335,617 B1 | 1/2002 | Osadchy et al. |
| 6,366,799 B1 | 4/2002 | Acker et al. |
| 6,373,240 B1 | 4/2002 | Govari |
| 6,427,314 B1 | 8/2002 | Acker |
| 6,453,190 B1 | 9/2002 | Acker et al. |
| 6,484,118 B1 | 11/2002 | Govari |
| 6,558,333 B2 | 5/2003 | Gilboa et al. |
| 6,574,498 B1 | 6/2003 | Gilboa |
| 6,580,938 B1 | 6/2003 | Acker |
| 6,591,129 B1 | 7/2003 | Ben-Haim et al. |
| 6,593,884 B1 | 7/2003 | Gilboa et al. |
| 6,615,155 B2 | 9/2003 | Gilboa |
| 6,618,612 B1 | 9/2003 | Acker et al. |
| 6,650,927 B1 | 11/2003 | Keidar |
| 6,690,816 B2 | 2/2004 | Aylward et al. |
| 6,690,963 B2 | 2/2004 | Ben-Haim et al. |
| 6,702,780 B1 | 3/2004 | Gilboa et al. |
| 6,711,429 B1 | 3/2004 | Gilboa et al. |
| 6,788,967 B2 | 9/2004 | Ben-Haim et al. |
| 6,833,814 B2 | 12/2004 | Gilboa et al. |
| 6,947,788 B2 | 9/2005 | Gilboa et al. |
| 6,995,729 B2 | 2/2006 | Govari et al. |
| 6,996,430 B1 | 2/2006 | Gilboa et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,366,562 B2 | 4/2008 | Dukesherer et al. |
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,517,318 B2 * | 4/2009 | Altmann et al. ............. 600/459 |
| 7,831,076 B2 * | 11/2010 | Altmann et al. ............. 382/128 |
| 2001/0031919 A1 | 10/2001 | Strommer et al. |
| 2002/0193686 A1 | 12/2002 | Gilboa |
| 2003/0074011 A1 | 4/2003 | Gilboa et al. |
| 2003/0099390 A1 | 5/2003 | Zeng et al. |
| 2003/0216639 A1 | 11/2003 | Gilboa et al. |
| 2004/0097804 A1 | 5/2004 | Sobe |
| 2004/0138548 A1 | 7/2004 | Strommer et al. |
| 2004/0249267 A1 | 12/2004 | Gilboa |
| 2005/0033149 A1 | 2/2005 | Strommer et al. |
| 2005/0107688 A1 | 5/2005 | Strommer |
| 2005/0197566 A1 | 9/2005 | Strommer et al. |
| 2006/0058647 A1 | 3/2006 | Strommer et al. |
| 2006/0064006 A1 | 3/2006 | Strommer et al. |

(Continued)

OTHER PUBLICATIONS

WIPO, U.S. International Search Authority, International Search Report and Written Opinion mailed Sep. 24, 2009 in International Patent Application No. PCT/IL2009/000569, 7 pages.

(Continued)

*Primary Examiner* — Tu Nguyen
(74) *Attorney, Agent, or Firm* — Inskeep IP Group, Inc.

(57) ABSTRACT

A registration method whereby a sensor-based approach is used to establish initial registration and whereby upon the commencement of navigating an endoscope, image-based registration methods are used in order to more accurately maintain the registration between the endoscope location and previously-acquired images. A six-degree-of-freedom location sensor is placed on the probe in order to reduce the number of previously-acquired images that must be compared to a real-time image obtained from the endoscope.

8 Claims, No Drawings

U.S. PATENT DOCUMENTS

| | | |
|---|---|---|
| 2007/0167738 A1 | 7/2007 | Timinger et al. |
| 2007/0167743 A1 | 7/2007 | Honda et al. |
| 2007/0167806 A1 | 7/2007 | Wood et al. |
| 2007/0287901 A1 | 12/2007 | Strommer et al. |
| 2008/0033452 A1 | 2/2008 | Vetter et al. |
| 2008/0086051 A1 | 4/2008 | Voegele |
| 2008/0097187 A1 | 4/2008 | Gielen et al. |
| 2008/0118135 A1 | 5/2008 | Averbuch et al. |
| 2008/0132909 A1 | 6/2008 | Jascob et al. |
| 2008/0132911 A1 | 6/2008 | Sobe |
| 2008/0139915 A1 | 6/2008 | Dolan et al. |
| 2008/0147000 A1 | 6/2008 | Seibel et al. |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2008/0247622 A1 | 10/2008 | Aylward et al. |

OTHER PUBLICATIONS

United States Patent and Trademark Office, Final Office Action mailed Nov. 4, 2011 in U.S. Appl. No. 11/939,537, 22 pages.

United States Patent and Trademark Office, Office Action mailed Apr. 1, 2011 in U.S. Appl. No. 11/939,537, 21 pages.

WIPO, U.S. International Search Authority, International Search Report and Written Opinion mailed Nov. 13, 2008 in International Patent Application No. PCT/IB07/04567, 8 pages.

Schmarak, Itzhak, Gera Strommer and Uzi Eichler, U.S. Appl. No. 10/986,567 filed Nov. 10, 2004, specification and drawings as filed, 81 pages.

* cited by examiner

HYBRID REGISTRATION METHOD

RELATED APPLICATIONS

This application claims priority to U.S. Provisional Application Ser. No. 61/059,669 filed Jun. 6, 2008 entitled Hybrid Registration Method, which is hereby incorporated herein by reference.

BACKGROUND OF THE INVENTION

Breakthrough technology has emerged which allows the navigation of a catheter tip through a tortuous channel, such as those found in the pulmonary system, to a predetermined target. This technology compares the real-time movement of a sensor against a three-dimensional digital map of the targeted area of the body (for purposes of explanation, the pulmonary airways of the lungs will be used hereinafter, though one skilled in the art will realize the present invention could be used in any body cavity or system: circulatory, digestive, pulmonary, to name a few).

Such technology is described in U.S. Pat. Nos. 6,188,355; 6,226,543; 6,558,333; 6,574,498; 6,593,884; 6,615,155; 6,702,780; 6,711,429; 6,833,814; 6,947,788; and 6,996,430, all to Gilboa or Gilboa et al.; and U.S. Published Applications Pub. Nos. 2002/0193686; 2003/0074011; 2003/0216639; 2004/0249267 to either Gilboa or Gilboa et al. All of these references are incorporated herein in their entireties.

Using this technology begins with recording a plurality of images of the applicable portion of the patient, for example, the lungs. These images are often recorded using CT technology. CT images are two-dimensional slices of a portion of the patient. After taking several, parallel images, the images may be "assembled" by a computer to form a three-dimensional model, or "CT volume" of the lungs.

The CT volume is used during the procedure as a map to the target. The physician navigates a steerable probe that has a trackable sensor at its distal tip. The sensor provides the system with a real-time image of its location. However, because the image of the sensor location appears as a vector on the screen, the image has no context without superimposing the CT volume over the image provided by the sensor. The act of superimposing the CT volume and the sensor image is known as "registration."

Sensor Probe-Based Registration Methods

There are various registration methods, some of which are described in the aforementioned references, and utilize a probe with a trackable sensor, as described above. For example, point registration involves selecting a plurality of points, typically identifiable anatomical landmarks, inside the lung from the CT volume and then using the sensor (with the help of an endoscope) and "clicking" on each of the corresponding landmarks in the lung. Clicking on the landmarks refers to activating a record feature on the sensor that signifies the registration point should be recorded. The recorded points are then aligned with the points in the CT volume, such that registration is achieved. This method works well for initial registration in the central area but as the sensor is navigated to the distal portions of the lungs, the registration becomes less accurate as the distal airways are smaller. Also, the point registration method matches a "snapshot" location of the landmarks to another "snapshot" (CT volume) of the lungs. Each snapshot is taken at different times and, potentially, at different points in the breathing cycle. Due to the dynamic nature of the lungs, the shape of the lungs during the CT scan is likely not the same as the shape of those same lungs during the procedure. Moreover, because the physician is "clicking" on the landmarks over the course of several breathing cycles, it is up to the physician to approximate the timing of his clicking so that it roughly matches the point in the breathing cycle at which the CT scan was taken. This leaves much room for error. Finally, it is time consuming for the physician to maneuver the sensor tip to the various landmarks.

Another example of a registration method utilizing a trackable sensor involves recording a segment of an airway and shape-match that segment to a corresponding segment in the CT volume. This method of registration suffers similar setbacks to the point registration method, though it can be used in more distal airways because an endoscope is not required. The registration should be conducted more than once to keep the registration updated. It may be inconvenient or otherwise undesirable to require additional registration steps from a physician. Additionally, this method requires that a good image exists in the CT volume for any given airway occupied by the sensor. If for example, the CT scan resulted in an airway shadowed by a blood vessel, for example, the registration will suffer because the shape data on that airway is compromised.

Another registration method tailored for trackable sensors is known as "Adaptive Navigation" and was developed and described in U.S. Published Application 2008/0118135 to Averbuch et al., incorporated by reference herein in its entirety. This registration technique operates on the assumption that the sensor remains in the airways at all times. The position of the sensor is recorded as the sensor is advanced, thus providing a shaped historical path of where the sensor has been. This registration method requires the development of a computer-generated and automatically or manually segmented "Bronchial Tree" (BT). The shape of the historical path is matched to a corresponding shape in the BT.

Segmenting the BT involves converting the CT volume into a series of digitally-identified branches to develop, or "grow," a virtual model of the lungs. Automatic segmentation works well on the well-defined, larger airways and smaller airways that were imaged well in the CT scans. However, as the airways get smaller, the CT scan gets "noisier" and makes continued automatic segmentation inaccurate. Noise results from poor image quality, small airways, or airways that are shadowed by other features such as blood vessels. Noise can cause the automatic segmentation process to generate false branches and/or loops—airways that rejoin, an occurrence not found in the actual lungs.

Another registration method is herein referred to as "feature-based registration." When the CT scans are taken, the CT machine records each image as a plurality of pixels. When the various scans are assembled together to form a CT volume, voxels (volumetric pixels) appear and can be defined as volume elements, representing values on a regular grid in three dimensional space. Each of the voxels is assigned a number based on the tissue density Housefield number. This density value can be associated with gray level or color using well known window-leveling techniques.

The sensing volume of the electromagnetic field of the sensor system is also voxelized by digitizing it into voxels of a specific size compatible with the CT volume. Each voxel visited by the sensor can be assigned a value that correlates to the frequency with which that voxel is visited by the sensor. The densities of the voxels in the CT volume are adjusted according to these values, thereby creating clouds of voxels in the CT volume having varying densities. These voxels clouds or clusters thus match the interior anatomical features of the lungs.

By using a voxel-based approach, registration is actually accomplished by comparing anatomical cavity features to cavity voxels, as opposed to anatomical shapes or locations to structure shapes or locations. An advantage of this approach is that air-filled cavities are of a predictable range of densities.

Image-Based Registration Methods

Some registration methods are used with systems that use a bronchoscope without a trackable sensor. One of these registration methods compares an image taken by a video camera to a virtual model of the airways. The virtual model includes surfaces, reflections and shadows. This method while herein be referred to as "virtual surface matching." A virtual camera is established to generate a viewpoint and a virtual light source is used to provide the reflections, shadows, and surface texture. The virtual camera and light source are matched to the actual video camera and light source so that an "apples to apples" comparison can be performed. Essentially, the virtual model is a library of thousands of computer-generated images of the lungs, from various viewpoints. Hence, the image taken by the video camera is compared against this large library, in the same way a fingerprint is lifted from a crime scene and compared against a large database of fingerprint images. Once the match is found, the camera is determined to be where the "virtual camera" was when the computer image was generated.

One problem with this method is that each time the camera moves, as it is being advanced toward the target, the images recorded by the camera are compared against the large library of computer generated images. This is time consuming and places a strain on the computer resources. It also presents the risk that there may be more than one computer-generated image that closely matches the actual image. For example, if the video camera is up against an airway wall, there may not be much on the image to distinguish it from other similar computer generated images of walls.

Another problem is lack of tracking. Without a sensor, there is no recorded history. Hence, even though the camera is moving and being registered, as soon as the camera encounters an area that matches more than one computer generated image, the registration is lost. The system has no capacity for "tracking" the movement of the camera. In other words, the system does not look at the previous matches to deduce which of the possible images is likely to be the correct one.

Yet another bronchoscope registration method involves terrain or skeletal surface-matching. The virtual model of the lungs is left in a skeletal format, rather than filling the contours in with surfaces and reflections. This saves on initial processing time. As video images are captured of the actual lungs, they are converted into skeletal, digital images. The "real" skeletal images are then matched against the virtual skeletal images. This method requires more processing of the video images than the previously described "virtual surface geometery matching" method but the matching steps are accomplished much more quickly because each of the virtual images is smaller in terms of data. Like the virtual surface matching method, this method present the risk that there may be more than one computer-generated image that closely matches the acquired image, such as when the camera is pointing at a wall.

Each of the aforementioned registration methods has advantages and disadvantages over the others. Generally, the methods using trackable sensors are more accurate than the image-based methods. More particularly, the methods using trackable sensors are more accurate "globally," that is, they are more accurate when it comes to indicating the present position on a scan of the entire lungs. Image-based methods, on the other hand, can be more accurate "locally," that is, they can be more accurate relative to a small area, if conditions are optimal. Thus, it would be advantageous to introduce a hybrid method that utilizes the advantages of all of the aforementioned methods.

BRIEF SUMMARY OF THE INVENTION

The present invention provides several new or improved registration methods. Additionally, the present invention describes a concept whereby a most accurate registration is determined and utilized at any given time during a procedure, thereby utilizing the advantages of all of the aforementioned registration methods.

More specifically, one aspect of the present invention provides a method of registering real-time sensor location data to previously acquired images of a branched network of body lumens. This method involves placing a probe containing a sensor at a distal end thereof into a branched network of body lumens in a patient; performing an initial registration between a real-time sensor location and a previously acquired image selected a plurality of previously acquired images of said branched network; receiving data from said sensor to determine an approximate location of said sensor; using said approximate location of said sensor to create a subgroup of said plurality of images, said subgroup containing one or more previously acquired images corresponding to said approximate location; and selecting an image from said subgroup that most accurately corresponds to said approximate location to update said initial registration using an image-based registration technique.

Placing a probe containing a sensor at a distal end thereof may comprise placing a probe with a six degree of freedom sensor at a distal end thereof.

Performing an initial registration may comprise viewing a landmark through an endoscope; using data from said sensor to project a beam from a tip of said probe to said landmark; displaying said beam on a monitor; calculating and recording coordinates of said beam location on said landmark; and using said coordinates as a registration point.

Receiving data from said sensor to determine a proximate location of said sensor may comprise receiving six degree of freedom data from said sensor.

Placing a probe containing a sensor at a distal end thereof into a branched network of body lumens may comprise placing a bronchoscope containing a sensor at a distal end thereof into said branched network of body lumens.

Selecting an image from said subgroup that most accurately corresponds to said approximate location to update said initial registration using an image-based registration technique may comprise selecting an image from said subgroup that most closely matches an image being viewed through said bronchoscope.

Performing an initial registration between a real-time sensor location and a previously acquired image selected a plurality of previously acquired images of said branched network may comprise performing an initial registration using a 4D registration technique.

Performing an initial registration using a 4D registration technique may comprise: recording an image of a landmark as it moves through at least one breathing cycle; recording concurrently a position of said sensor; recording concurrently positions of patient sensors, said patient sensor attached at various locations on said patient; saving said recordings as a data set for said landmark; and using said data set to correlate said position of said sensor to a previously acquired image of said branched network of body lumens.

Another aspect of the present invention provides method of navigating a probe through a branched network of lumens of a patient comprising: compiling a database of images of said branched network of lumens prior to a navigating procedure; placing a probe containing a sensor at a distal end thereof into said branched network; receiving probe location data from said sensor; and using at least said probe location data to select an image from said database to display to a user navigating said probe, said image being representative of a location of said probe.

Compiling a database of images of said branched network of lumens prior to a navigating procedure may comprise compiling a plurality of CT scans.

Placing a probe containing a sensor at a distal end thereof into said branched network may comprise placing a probe containing a six degree of freedom sensor at a distal end thereof into said branched network.

Placing a probe containing a sensor at a distal end thereof into said branched network may comprise placing an endoscope containing a sensor at a distal end thereof into said branched network.

Receiving probe location data from said sensor may comprise receiving said probe's location and orientation from said sensor.

Using at least said probe location data to select an image from said database to display to a user navigating said probe, said image being representative of a location of said probe may comprise using said probe location data to create a subgroup of images from said database, said subgroup containing only images that correspond to a vicinity of said probe location.

Placing a probe containing a sensor at a distal end thereof into said branched network may comprise placing an endoscope containing a sensor at a distal end thereof into said branched network.

Using at least said probe location data to select an image from said database to display to a user navigating said probe, said image being representative of a location of said probe further may comprise matching a real-time image from said endoscope to an image from said subgroup.

Another aspect of the present invention provides a method of registering real-time sensor location data to previously acquired images of a branched network of body lumens comprising: placing a probe containing a sensor at a distal end thereof in branched network of body lumens in a patient; placing a plurality of patient sensors on said patient; recording an image of an anatomical landmark in said patient as said landmark moves through at least one breathing cycle; recording concurrently a position of said sensor; recording concurrently positions of patient sensors, said patient sensor attached at various locations on said patient; saving said recordings as a data set for said landmark; and using said data set to correlate said position of said sensor to a previously acquired image of said branched network of body lumens.

Placing a plurality of patient sensors on said patient may comprise affixing said plurality of patient sensors to said patient's chest or affixing a plurality of patient sensors to said branched network.

Using said data set to correlate said position of said sensor to a previsouly acquired image of said branched network of body lumens may comprise using said data set to correlate said position of said sensor to a previously acquired CT image of said branched network of body lumens.

DESCRIPTION OF THE INVENTION

The sensor based and image-based registration methods described above are improved upon by combining the advantages of each. Put another way, the image-based registration techniques are improved upon through the use of a trackable sensor. By monitoring sensor data, an approximate position of the probe tip is easily determined. Hence, a database of virtual images may be appropriately parsed such that the matching algorithm has a significantly reduced number of iterations through which it must cycle to find a match. The position of the sensor is thus used as filtering tool to determine which images are locally relevant.

Additionally, the tracking of a tool tip or bronchoscope location will not be lost in cases of partial or complete obscurity of the video image or in cases when the bronchoscope is passing a bifurcation while the camera is pointed away from the bifurcation toward a wall. Due to the tracking capability provided by the trackable sensor, the number of matching images will typically be reduced to only one after the outliers are removed. Hence, not only is the matching procedure much quicker, it is also more accurate and less likely to provide incorrect matches.

The image-based registration methods are further improved because the need for camera calibration is eliminated. Presently, image-based registration methods require extensive camera calibration efforts, prior to each procedure, in order to obtain images that can be matched to the virtual images. Factors such as camera angle and camera distortion must be corrected prior to the matching process. Because the use of the trackable sensor as an additional modality greatly reduces the amount of data involved, calibration is much less crucial. In other words, despite forgoing the calibration step, a match is still likely to be found and accurate because the number of images the camera image is being compared to is greatly reduced.

The point registration method described above is also improved by the present invention. Recall that presently the point registration method is comprised of two general steps: 1) finding a predetermined anatomical landmark using a bronchoscope and 2) "click" on the landmark by advancing the probe with the trackable sensor until it touches the landmark, then press a button that records the three-dimensional coordinates of the landmark. The present invention obviates the need for the second step by utilizing the six degree of freedom data provided by the sensor once the landmark is being viewed through the bronchoscope. This data is used to project a virtual "beam" from the tip of the probe to the target. The virtual beam appears on the monitor and the physician is then able to record the coordinates of the landmark without actually having to maneuver the probe into physical contact with the landmark.

The present invention also provides a novel registration method, herein referred to as "4D registration." Rather than clicking on a landmark at an approximated point in the breathing cycle, video registration involves recording an image of a landmark as it moves through at least one, preferably two or more, breathing cycles. The recording of the landmark includes a recording of the position of the trackable sensor as well as the positions of the patient sensors. This way, rather than acquiring a single data coordinate for each landmark, an entire data set is recorded for each landmark over a period of time and including all or most of the possible lung positions. This way lung movement may be taken into account during the registration process. Furthermore, the matching error will be minimized if an entire data set is used for each point, rather than a single, three-dimensional coordinate.

For example, assume three registration areas are being monitored. The positions of all three are recorded over three separate intervals. The patient sensor positions are also being recorded during each of these intervals as well as the position of the trackable sensor and attached to each image frame. After the three registration points have been recorded over one or more breathing cycles, they are aligned using the patient sensor positions as an indication of the breathing cycle. Hence, for most of the positions of the patient sensors (extremes excepted), there will be a corresponding position of each of the sensors. Hence, the three intervals during which the recordings were taken are "superimposed" so to speak, as though they were all recorded simultaneously. Later, during the procedure, the patient sensor positions are used as an indication of breathing cycle and it can be determined at which phase of the breathing cycle the registration is most accurate. Moreover, this information can be utilized during navigation by giving the higher weight to sensor data acquired in a specific phase of breathing.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

We claim:

1. A method of registering real-time sensor location data to previously acquired images of a branched network of body lumens comprising:
   placing a probe containing a sensor at a distal end thereof into a branched network of body lumens in a patient;
   performing an initial registration between a real-time sensor location and a previously acquired image selected a plurality of previously acquired images of said branched network;
   receiving data from said sensor to determine an approximate location of said sensor;
   using said approximate location of said sensor to create a subgroup of said plurality of images, said subgroup containing one or more previously acquired images corresponding to said approximate location; and,
   selecting an image from said subgroup that most accurately corresponds to said approximate location to update said initial registration using an image-based registration technique.

2. The method of claim 1 wherein placing a probe containing a sensor at a distal end thereof comprises placing a probe with a six degree of freedom sensor at a distal end thereof.

3. The method of claim 2 wherein performing an initial registration comprises:
   viewing a landmark through an endoscope;
   using data from said sensor to project a beam from a tip of said probe to said landmark;
   displaying said beam on a monitor;
   calculating and recording coordinates of said beam location on said landmark; and,
   using said coordinates as a registration point.

4. The method of claim 1 wherein receiving data from said sensor to determine a proximate location of said sensor comprises receiving six degree of freedom data from said sensor.

5. The method of claim 1 wherein placing a probe containing a sensor at a distal end thereof into a branched network of body lumens comprises placing a bronchoscope containing a sensor at a distal end thereof into said branched network of body lumens.

6. The method of claim 5 wherein selecting an image from said subgroup that most accurately corresponds to said approximate location to update said initial registration using an image-based registration technique comprises selecting an image from said subgroup that most closely matches an image being viewed through said bronchoscope.

7. The method of claim 1 wherein performing an initial registration between a real-time sensor location and a previously acquired image selected a plurality of previously acquired images of said branched network comprises performing an initial registration using a 4D registration technique.

8. The method of claim 7 wherein performing an initial registration using a 4D registration technique comprises:
   recording an image of a landmark as it moves through at least one breathing cycle;
   recording concurrently a position of said sensor;
   recording concurrently positions of patient sensors, said patient sensor attached at various locations on said patient;
   saving said recordings as a data set for said landmark; and,
   using said data set to correlate said position of said sensor to a previously acquired image of said branched network of body lumens.

* * * * *